US008916719B2

(12) United States Patent
Shaikh et al.

(10) Patent No.: US 8,916,719 B2
(45) Date of Patent: Dec. 23, 2014

(54) PROCESS FOR PRODUCING DRY PURIFIED FURAN-2,5-DICARBOXYLIC ACID WITH OXIDATION OFF-GAS TREATMENT (71) Applicant: Eastman Chemical Company, Kingsport, TN (US)

(72) Inventors: Ashfaq Shahanawaz Shaikh, Kingsport, TN (US); Kenny Randolph Parker, Afton, TN (US); Mesfin Ejerssa Janka, Kingsport, TN (US); Lee Reynolds Partin, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 13/798,235

(22) Filed: Mar. 13, 2013

(65) Prior Publication Data

US 2014/0142326 A1 May 22, 2014

Related U.S. Application Data (60) Provisional application No. 61/728,314, filed on Nov. 20, 2012.

(51) Int. Cl.
*C07D 307/68* (2006.01)
*F01K 27/00* (2006.01)

(52) U.S. Cl.
CPC .............. *C07D 307/68* (2013.01); *F01K 27/00* (2013.01)
USPC ........................................................ 549/485

(58) Field of Classification Search
CPC .................................................... C07D 307/68
USPC ........................................................ 549/485
See application file for complete search history.

(56) References Cited

U.S. PATENT DOCUMENTS

| | | | |
|---|---|---|---|
| 2,797,197 | A | 6/1957 | Thompson et al. |
| 3,203,963 | A | 8/1965 | Hales et al. |
| 3,326,944 | A | 6/1967 | Lew |
| 4,977,283 | A | 12/1990 | Leupold et al. |
| 6,737,481 | B1 | 5/2004 | Kurian et al. |
| 7,052,764 | B2 | 5/2006 | Chang et al. |
| 7,385,081 | B1 | 6/2008 | Gong |
| 7,411,078 | B2 | 8/2008 | Miura et al. |
| 7,572,925 | B2 | 8/2009 | Dumesic et al. |
| 7,700,788 | B2 | 4/2010 | Lilga et al. |
| 8,183,020 | B2 | 5/2012 | Hanke |
| 8,193,381 | B2 | 6/2012 | Lilga et al. |
| 8,193,382 | B2 | 6/2012 | Lilga et al. |
| 8,748,479 | B2 | 6/2014 | Shaikh et al. |
| 2003/0055271 | A1 | 3/2003 | Grushin et al. |
| 2006/0205977 | A1 | 9/2006 | Sumner, Jr. et al. |
| 2007/0232815 | A1 | 10/2007 | Miura et al. |
| 2009/0124829 | A1 | 5/2009 | Gong |
| 2009/0131690 | A1 | 5/2009 | Gruter et al. |
| 2009/0156841 | A1 | 6/2009 | Sanborn et al. |
| 2009/0326262 | A1 | 12/2009 | Wan |
| 2010/0210867 | A1 | 8/2010 | Bustamante et al. |
| 2011/0092720 | A1 | 4/2011 | Yutaka et al. |

FOREIGN PATENT DOCUMENTS

| | | |
|---|---|---|
| CZ | 87340 | 7/1959 |
| EP | 1 834 951 A1 | 9/2007 |
| EP | 2 197 868 B1 | 4/2011 |
| EP | 2 197 865 B1 | 8/2012 |
| JP | 2007-261986 A | 10/2007 |
| JP | 2007-261990 A | 10/2007 |
| JP | 2009-001519 A | 1/2009 |
| JP | 2009-013079 A | 1/2009 |
| JP | 2009-242312 A | 10/2009 |
| SU | 162962 A | 9/1962 |
| WO | WO 02/098836 A1 | 12/2002 |
| WO | WO 2007/092183 A2 | 8/2007 |
| WO | WO 2008/054804 A2 | 5/2008 |
| WO | WO 2009/023174 A2 | 2/2009 |
| WO | WO 2009/030506 A4 | 3/2009 |
| WO | WO 2009/030507 A4 | 3/2009 |
| WO | WO 2010/077133 A1 | 7/2010 |
| WO | WO 2010/132740 A2 | 11/2010 |
| WO | WO 2011/043660 A2 | 4/2011 |
| WO | WO 2012/161968 A1 | 11/2012 |

OTHER PUBLICATIONS

Office Action dated Jun. 6, 2013 received in co-pending U.S. Appl. No. 13/228,809.
Office Action dated Jun. 6, 2013 received in co-pending U.S. Appl. No. 13/228,816.
PCT International Search Report and Written Opinion dated Jul. 29, 2013 for International Application No. PCT/US2013/044935.
PCT International Search Report and Written Opinion dated Aug. 9, 2013 for International Application No. PCT/US2013/044932.
Office Action dated Sep. 30, 2013 received in co-pending U.S. Appl. No. 13/758,070.
Office Action dated Sep. 30, 2013 received in co-pending U.S. Appl. No. 13/758,080.
Moldenhauer, et al., "Beitrage zur Furanchemie I", Justus Liebigs Annalen Der Chemie, vol. 580, 1953, pp. 169-190.
Office Action dated Oct. 25, 2013 received in co-pending U.S. Appl. No. 13/228,813.
PCT International Search Report and Written Opinion dated Oct. 31, 2013 for International Application No. PCT/US2013/050799.
Office Action dated Nov. 5, 2013 received in co-pending U.S. Appl. No. 13/228,797.
Office Action dated Nov. 8, 2013 received in co-pending U.S. Appl. No. 13/758,070.
Office Action dated Nov. 12, 2013 received in co-pending U.S. Appl. No. 13/228,799.
Office Action dated Nov. 14, 2013 received in co-pending U.S. Appl. No. 13/228,809.

(Continued)

*Primary Examiner* — Taofiq A Solola
(74) *Attorney, Agent, or Firm* — Steven A. Owen (57) ABSTRACT

Disclosed is a process for producing a dry, purified carboxylic acid product comprising furan-2,5-dicarboxylic acid (FDCA). Also disclosed is a method for treating an oxidation off-gas stream from such a process. The method features solvent as well as energy recovery from the off-gas stream.

10 Claims, 2 Drawing Sheets

(56) References Cited

OTHER PUBLICATIONS

Office Action dated Nov. 18, 2013 received in co-pending U.S. Appl. No. 13/758,088.
Co-pending U.S. Appl. No. 14/084,165, filed Nov. 19, 2013, Ashfaq Shaikh et al.
PCT International Search Report and Written Opinion dated Nov. 28, 2013 for International Application No. PCT/US2013/050794.
Office Action dated Dec. 13, 2013 received in co-pending U.S. Appl. No. 13/228,816.
Office Action dated Dec. 16, 2013 received in co-pending U.S. Appl. No. 13/553,976.
Slavinskaya, V. A., et al., "Liquid-Phase Catalytic Oxidation of 5-Methylfurfural," React. Kinet. Catal. Lett., 1979, vol. 11, No. 3, pp. 215-220.
Gandini, A., et al., "Rapid Communication: The Furan Counterpart of Polu(ethylene terephthalate); An Alternative Material Based on Renewable Resources," Journal of Polymer Science: Part A: Polymer Chemistry, 2009, vol. 47, pp. 295-298, Wiley Periodicals, Inc.
Partenheimer, W. et al., "Synthesis of 2,5-Diformylfuran and Furan-2,5-Dicarboxylic Acid by Catalytic Air-Oxidation of 5-Hydroxymethylfurfural, Unexpectedly Selective Aerobic Oxidation of Benzyl Alcohol to Benzaldehyde with Metal/Bromide Catalysts," Adv. Synth. Catal., 2001, vol. 343, No. 1, pp. 102-111.
Lewkowski, J., "Synthesis, Chemistry and Applications of 5-Hydroxymethylfurfural and its Derivatives," ARKIVOC, 2001, pp. 17-54.
Zakharov, I. V., "Mechanism of Initiation and Inhibition by Mn(II) in Hydrocarbon Oxidation in the Presence a Cobalt-Manganese Bromide Catalyst," Kinetics and Catalysis, 1998, vol. 39, No. 4, pp. 485-492.
Jiao, X. J. et al., "Kinetics of Manganese(III) Acetate in Acetic Acid: Generation of Mn(III) with Co(II), Ce(IV), and Dibromide Radicals; Reactions of Mn(III) with Mn(II), Co(II), Hydrogen Bromide, and Alkali Bromides," Inorg. Chem., 2000, vol. 39, pp. 1549-1554, American Chemical Society.
Copending U.S. Appl. No. 13/228,816, filed Sep. 9, 2011, Mesfin Ejerssa Janka, et al.
Copending U.S. Appl. No. 13/228,799 filed Sep. 9, 2011, Mesfin Ejerssa Janka, et al.
Copending U.S. Appl. No. 13/228,809, filed Sep. 9, 2011, Mesfin Ejerssa Janka, et al.
Copending U.S. Appl. No. 13/228,803, filed Sep. 9, 2011, Mesfin Ejerssa Janka, et al.
Copending U.S. Appl. No. 13/228,797, filed Sep. 9, 2011, Mesfin Ejerssa Janka, et al.
Copending U.S. Appl. No. 13/228,813, filed Sep. 9, 2011, Ashfaq Shaikh, et al.
PCT International Search Report and Written Opinion dated Jul. 27, 2012 for International Application No. PCT/US2012/037223.
PCT International Search Report and Written Opinion dated Aug. 7, 2012 for International Application No. PCT/US2012/037218.
PCT International Search Report and Written Opinion dated Jul. 27, 2012 for International Application No. PCT/US2012/037204.
PCT international Search Report and Written Opinion dated Jul. 27, 2012 for International Application No. PCT/US2012/037206.
PCT International Search Report and Written Opinion dated Aug. 3, 2012 for International Application No. PCT/US2012/037210.
Copending U.S. Appl. No. 13/553,976, filed Jul. 20, 2012, Mesfin Ejeresa Janka, et al.
PCT International Search Report and Written Opinion dated Aug. 23, 2012 for International Application No. PCT/US2012/037228.
Chheda et al., "Production of 5-hydromethylfurfural and furfural by dehydration of biomass-derived mono- and poly-*Saccharides*." Green Chemistry, vol. 9, pp. 342-350 (2007).
Werpy et al., "Top Value Assed Chemicals from Biomass" DOE (Pacific NW National Laboratory) (Aug. 2004).
Verevkin et al., "Biomass-Derived Platform Chemicals: Thermodynamic Studies on the Conversions of 5-Hydroxymethylfurfural into Bulk Intermediates", Ind. Eng. Chem. Res., vol. 48, pp. 10087-10093 (2009).
Manasek, Z., "Modification of a Fiber-Forming Polyester Based on 2.5-Furandicarboxylic Acid", Mar. 20, 1963, pp. 35-38, UDC 677. 465.
Rodivilova et al., "Synthesis and Investigation of Polyarylates Based on 2,5-Furandicarboxylic Acid and Diphenylolpropane", Khimiya I Khimicheskaya Tekhnologiya, No. 7, 1968, pp. 818-821.
Copending U.S. Appl. No. 13/758,070, filed Feb. 4, 2013, Kenny Randolph Parker, et al.
Copending application U.S. Appl. No. 13/758,080, filed Feb. 4, 2013, Mesfin Ejerssa Janka, et al.
Office Action dated Apr. 18, 2013 received in co-pending U.S. Appl. No. 13/228,797.
Office Action dated Apr. 18, 2013 received in co-pending U.S. Appl. No. 13/228,813.
Office Action dated Apr. 29, 2013 received in co-pending U.S. Appl. No. 13/228,799.
Office Action dated May 31, 2013 received in co-pending U.S. Appl. No. 13/228,803.
Notice of Allowance dated Apr. 1, 2014 received in co-pending U.S. Appl. No. 13/758,080.
Notice of Allowance dated Apr. 1, 2014 received in co-pending U.S. Appl. No. 13/758,070.
Office Action dated Apr. 17, 2014 received in co-pending U.S. Appl. No. 13/758,072.
Copending U.S. Appl. No. 14/259,754, filed Apr. 23, 2014, Ashfaq Shaikh et al.
Office Action dated Apr. 25, 2014 received in co-pending U.S. Appl. No. 13/228,797.
Office Action dated Apr. 25, 2014 received in co-pending U.S. Appl. No. 13/228,809.
Office Action dated Apr. 25, 2014 received in co-pending U.S. Appl. No. 13/798,257.
Notice of Allowance dated Apr. 28, 2014 received in co-pending U.S. Appl. No. 13/228,813.
Notice of Allowance dated Apr. 28, 2014 received in co-pending U.S. Appl. No. 13/228,803.
Notice of Allowance dated May 1, 2014 received in co-pending U.S. Appl. No. 13/228,799.
Notice of Allowance dated May 13, 2014 received in co-pending U.S. Appl. No. 13/758,088.
Office Action dated May 29, 2014 received in co-pending U.S. Appl. No. 13/228,816.
Notice of Allowance dated Jun. 11, 2014 received in co-pending U.S. Appl. No. 13/553,976.
Copending U.S. Appl. No. 14/309,010, filed Jun. 19, 2014, Janka et al.
Copending U.S. Appl. No. 14/317,588, filed Jun. 27, 2014, Parker et al.
Copending U.S. Appl. No. 14/317,692, filed Jun. 27, 2014, Janka et al.
Copending U.S. Appl. No. 14/317,782, filed Jun. 27, 2014, Parker et al.
Copending U.S. Appl. No. 14/317,875, filed Jun. 27, 2014, Janka et al.

PROCESS FOR PRODUCING DRY PURIFIED FURAN-2,5-DICARBOXYLIC ACID WITH OXIDATION OFF-GAS TREATMENT

CROSS-REFERENCES TO RELATED APPLICATION

This application claims priority to U.S. Provisional Application No. 61/728,314, filed 20 Nov. 2012, the disclosure of which is incorporated herein by reference in its entirety.

FIELD OF THE INVENTION

The invention generally relates to a process for producing dry, purified furan-2,5-dicarboxylic acid (FDCA). The invention also generally relates to a method for treating an oxidation zone off-gas stream from the process for producing FDCA.

BACKGROUND OF THE INVENTION

Aromatic dicarboxylic acids, such as terephthalic acid and isophthalic acid, are used to produce a variety of polyester products, important examples of which are poly(ethylene terephthalate) and its copolymers. These aromatic dicarboxylic acids are synthesized by the catalytic oxidation of the corresponding dialkyl aromatic compounds, which are obtained from fossil fuels. There is a growing interest in using renewable resources as feed stocks in the chemical industry, mainly due to the progressive reduction of fossil fuel reserves and their related environmental impact.

FDCA is a versatile intermediate considered as a promising bio-based alternative to terephthalic acid and isophthalic acid. Like aromatic diacids, FDCA can be condensed with diols such as ethylene glycol to make polyester resins similar to polyethylene terephthalate (PET). FDCA has been prepared by oxidizing 5-(hydroxymethyl) furfural (5-HMF) with air using homogenous catalysts, but only a maximum yield of 44.8% was reported using a Co/Mn/Br catalyst system and a maximum yield of 60.9% was reported using a Co/Mn/Br/Zr catalyst system.

Recently, we reported a process for producing FDCA in high yields by liquid-phase oxidation of 5-HMF using a Co/Mn/Br catalyst system. The process minimizes solvent and starting material loss through carbon burn (U.S. patent application Ser. No. 13/228,803, filed on Sep. 9, 2011; the entire content of which is hereby incorporated by reference).

Heterogeneous-catalyzed oxidation of 5-HMF using $ZrO_2$ mixed with platinum (II) acetylacetonate in water has also been reported (U.S. Pat. No. 7,700,788 B2), but due to FDCA's very low solubility in water, this process has to be conducted under very dilute conditions to avoid the FDCA from precipitating on the catalyst's surface, which makes the process uneconomical. Another heterogeneous-catalyzed oxidation of 5-HMF has been reported using molecular $O_2$ and a Pt/C catalyst (U.S. Pat. No. 4,977,283). High FDCA yield was achieved, but with the additional expense of feeding purified $O_2$ and continually adjusting pH via sodium hydroxide addition. The reaction product was the disodium salt of FDCA, which leads to a wasteful salt by-product in the conversion to FDCA.

In view of the above, there is a need in the art for a high-yield process for producing a dry, purified FDCA product (e.g., 90% FDCA yield). There is also a need in the art for a process for making FDCA that includes solvent and energy recovery from the oxidation zone off-gas stream.

The present invention aims to address these needs as well as others, which will become apparent from the following description and the appended claims.

SUMMARY OF THE INVENTION

The invention is as set forth in the appended claims.

Briefly, in one aspect, the present invention provides a method for treating an off-gas stream from a process for producing a carboxylic acid product comprising furan-2,5-dicarboxylic acid. The method comprises the steps of:

(a) providing an off-gas stream comprising an organic acid solvent vapor, water vapor, and an inert gas from a primary oxidation zone of a process for producing a carboxylic acid product comprising furan-2,5-dicarboxylic acid;

(b) passing the off-gas stream to a solvent recovery zone to condense and separate at least a portion of the organic acid solvent vapor and the water vapor to obtain a water-rich stream, a solvent-rich stream, and a high-energy inert gas stream;

(c) passing the high-energy inert gas stream to a power recovery zone to convert the high-energy inert gas stream to a low-energy inert gas stream and to generate an electrical power stream;

(d) passing the electrical power stream to a compression zone to convert a low-pressure gas stream comprising oxygen into a high-pressure gas stream comprising oxygen;

(e) passing the low-energy inert gas stream and a stream comprising an oxidizable fuel and oxygen to a thermal oxidation zone to combust at least a portion of organic compounds in the low-energy inert gas stream and generate a thermal oxidation gas stream; and (f) passing the thermal oxidation gas stream to a scrubbing zone to generate a treated off-gas stream and a liquid scrubbing effluent stream comprising water.

In another aspect, the present invention provides a process for producing a dry, purified carboxylic acid product comprising furan-2,5-dicarboxylic acid. The process comprises the steps of:

(A) providing a primary oxidation zone comprising a vapor phase and a liquid phase, the vapor phase comprising an inert gas and the liquid phase comprising an organic acid solvent and a catalyst system;

(A1) contacting a 5-(hydroxymethyl)furfural (5-HMF) compound with oxygen in the primary oxidation zone at conditions effective to oxidize the 5-HMF compound to form a crude product stream comprising furan-2,5-dicarboxylic acid (FDCA) and 5-formyl furan-2-carboxylic acid (FFCA), and a primary oxidation zone off-gas stream comprising organic acid solvent vapor, water vapor, and the inert gas;

(B) treating the primary oxidation zone off-gas stream according to a method comprising:

(B1) passing the primary oxidation zone off-gas stream to a solvent recovery zone to condense and separate at least a portion of the organic acid solvent vapor and the water vapor to obtain a water-rich stream, a solvent-rich stream, and a high-energy inert gas stream;

(B2) passing the high-energy inert gas stream to a power recovery zone to convert the high-energy inert gas stream to a low-energy inert gas stream and to generate an electrical power stream;

(B3) passing the electrical power stream to a compression zone to convert a low-pressure gas stream comprising oxygen into a high-pressure gas stream comprising oxygen;

(B4) passing the low-energy inert gas stream and a stream comprising an oxidizable fuel and oxygen to a thermal oxidation zone to combust at least a portion of organic compounds in the low-energy inert gas stream and generate a thermal oxidation gas stream; and (B5) passing the thermal oxidation gas stream to a scrubbing zone to generate a treated off-gas stream and a liquid scrubber effluent stream comprising water;

(C) passing at least a portion of the crude product stream to (a) a liquid displacement zone, and contacting the crude product stream with a solvent stream comprising fresh organic acid solvent in the liquid displacement zone to produce (i) a displaced mother liquor stream comprising the solvent, impurities, and catalyst components, and (ii) a low-impurity product stream comprising the FDCA and FFCA; (b) a secondary oxidation zone; or (c) both the liquid displacement zone and the secondary oxidation zone;

(D) passing the low-impurity product stream, if any, to the secondary oxidation zone, and contacting at least one of the low-impurity product stream and the crude product stream with oxygen in the secondary oxidation zone at conditions effective to oxidize the FFCA to form a secondary oxidation product stream comprising additional FDCA;

(E) passing at least a portion of the secondary oxidation product stream to a crystallization zone, a cooling zone, or both to produce a cooled, crystallized product stream;

(F) passing the cooled, crystallized product stream to a solid-liquid separation zone to (a) separate solids from liquids, (b) wash the separated solids with a wash solvent, and (c) reduce moisture in the washed solids to obtain a purified, de-watered wet cake stream and a solid-liquid separation mother liquor stream comprising the solvent, catalyst components, impurities, and oxidation products; and (G) passing the purified, de-watered wet cake stream to a drying zone to dry the wet cake stream and obtain a dry, purified carboxylic acid product comprising FDCA.

DETAILED DESCRIPTION OF THE INVENTION

In one aspect, the present invention provides a process for producing a dry, purified carboxylic acid product comprising furan-2,5-dicarboxylic acid (FDCA).

By "dry," it is meant that the product has less than 8 wt % of moisture. In preferred embodiments, the product may have less than 5 wt %, less than 1 wt %, less than 0.5 wt %, or less than 0.1 wt % of moisture.

By "purified," it is meant that the product has undergoing one or more purification steps.

Figure 1:
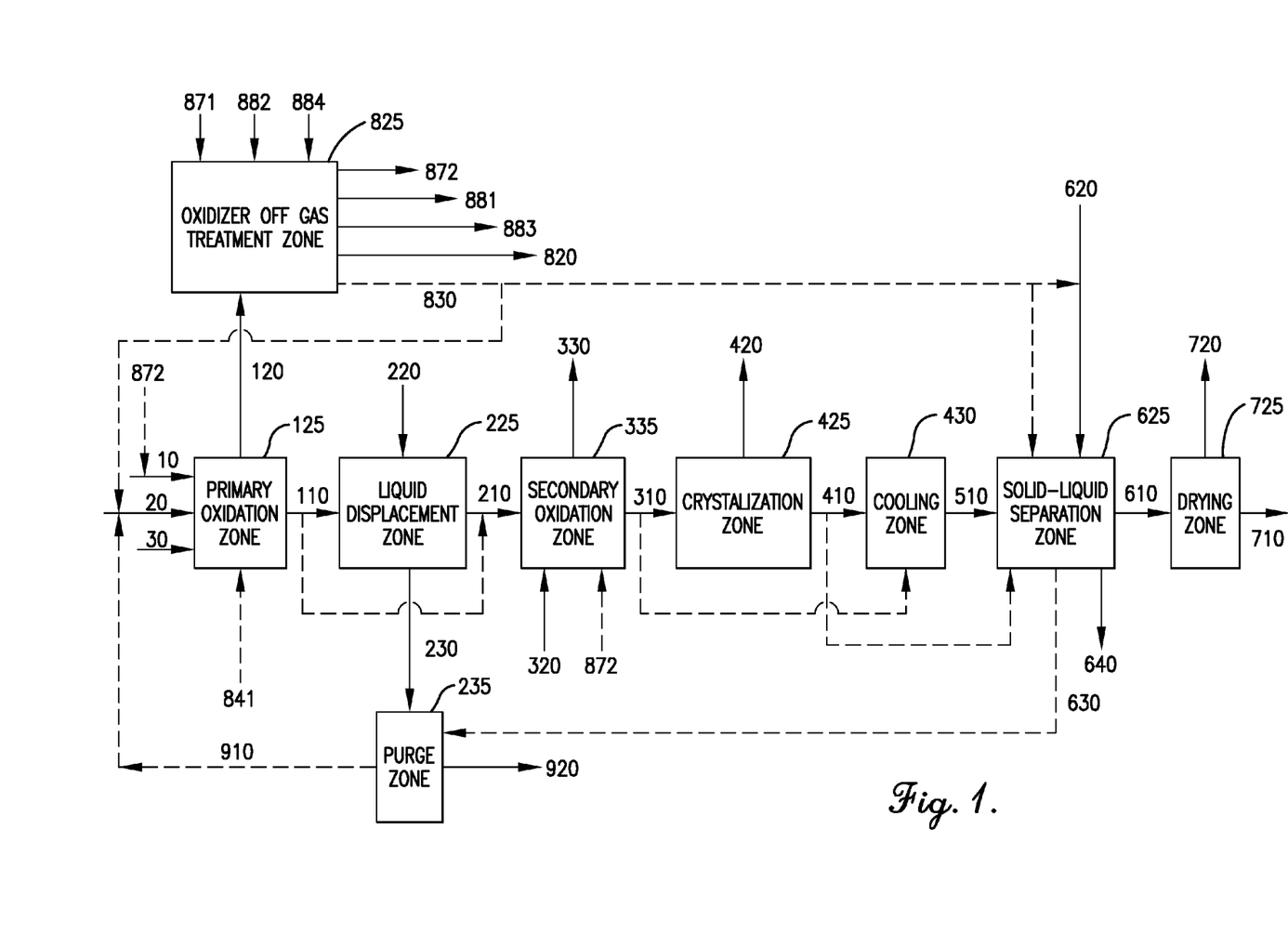
FIG. 1 is a flow diagram depicting a process for producing a dry, purified carboxylic acid product comprising FDCA according to the invention, where the dashed lines show optional embodiments.

FIG. 1 is a flow diagram depicting a process for producing a dry, purified carboxylic acid product comprising FDCA according to the invention, where the dashed lines show optional embodiments.

As seen in FIG. 1, the process according to the invention comprises (A) providing a primary oxidation zone 125. The primary oxidation zone 125, under reaction conditions, comprises a vapor phase and a liquid phase. The vapor phase comprises an inert gas such as nitrogen. The liquid phase comprises an organic acid solvent and an oxidation catalyst system. The primary oxidation zone 125 can have one or more oxidation reaction vessels. Each reactor will typically be characterized by a lower section where gas bubbles are dispersed in a continuous liquid phase. Solids can also be present in the lower section. In the upper section of the reactor, gas is in the continuous phase and entrained liquid drops can also be present.

Suitable organic acid solvents include aliphatic mono-carboxylic acids, preferably those containing 2 to 6 carbon atoms such as acetic acid, propionic acid, n-butyric acid, isobutyric acid, pentanoic acid, dimethylpropanoic acid, and hexanoic acid. The solvent may be a mixture of acids and may contain water. Preferably, the solvent comprises acetic acid.

Suitable catalyst systems comprise one or more cobalt, bromine, and manganese compounds that are soluble in the selected oxidation solvent. Preferably, the weight ratio of cobalt to manganese in the liquid reaction mixture ranges from 10 to 400, and the weight ratio of cobalt to bromine in the liquid reaction mixture ranges from 0.7 to 3.5. Generally, the amount of cobalt can range from 1,000 ppm to 6,000 ppm; the amount of manganese can range from 2 ppm to 600 ppm; and the amount of bromine can range from 300 ppm to 4,500 ppm based on the total weight of the liquid in the reaction medium of the primary oxidation zone 125.

The cobalt atoms may be provided in ionic form as inorganic cobalt salts, such as cobalt bromide, cobalt nitrate, or cobalt chloride; or as organic cobalt compounds such as cobalt salts of aliphatic or aromatic acids having 2-22 carbon atoms, including cobalt acetate, cobalt octanoate, cobalt benzoate, cobalt acetylacetonate, and cobalt naphthalate.

The oxidation state of cobalt when added as a compound to the reaction mixture is not limited, and includes both the +2 and +3 oxidation states.

The manganese atoms may be provided as one or more inorganic manganese salts, such as manganese borates, manganese halides, or manganese nitrates; or as organometallic manganese compounds such as the manganese salts of lower aliphatic carboxylic acids, including manganese acetate, and manganese salts of beta-diketonates, including manganese acetylacetonate.

The bromine component may be added as elemental bromine, in combined form, or as an anion. Suitable sources of bromine include hydrobromic acid, sodium bromide, ammonium bromide, potassium bromide, and tetrabromoethane. Hydrobromic acid, or sodium bromide may be preferred bromine sources.

The process according to the invention next comprises (A1) contacting a 5-(hydroxymethyl)furfural (5-HMF) compound with oxygen in the primary oxidation zone 125 at conditions effective to oxidize the 5-HMF compound to form a crude product stream 110 comprising furan-2,5-dicarboxylic acid (FDCA) and 5-formyl furan-2-carboxylic acid (FFCA), and a primary oxidation zone off-gas stream 120 comprising the organic acid solvent vapor, water vapor, and the inert gas.

The 5-HMF compound may be selected from 5-HMF itself, 5-HMF esters of the formula 5-R(CO)OCH$_2$-furfural, 5-HMF ethers of the formula 5-R'OCH$_2$-furfural, and 5-alkyl furfurals of the formula 5-R"-furfural; where R, R', and R"=alkyl, cycloalkyl, or aryl. The 5-HMF compound may be a mixture of 5-HMF and 5-HMF esters, a mixture of 5-HMF and 5-HMF ethers, or a mixture of 5-HMF and 5-alkyl furfurals.

Preferred 5-HMF compounds include those having the following chemical structures:

Preferred 5-HMF Derivative Feeds

The oxygen in the primary oxidation zone 125 may be sourced from an oxygen-containing gas, such as air, purified air, oxygen-enriched air, or even pure oxygen gas. The amount of oxygen in the primary oxidation zone 125 can range from 5 to 45 mole %, from 5 to 60 mole %, or from 5 to 80 mole %.

The temperature in the primary oxidation zone 125 can range from 105° C. to 180° C., or preferably from 110° C. to 160° C. The pressure in the primary oxidation zone 125 can range from 0.2 to 1.6 MPa, or preferably from 0.2 to 1.0 MPa. One advantage of the disclosed primary oxidation zone conditions is low carbon burn, as illustrated in Table 1.

In the primary oxidation zone 125, the 5-HMF or its derivatives are oxidized with elemental $O_2$ in a multi-step reaction to form FDCA with 5-formyl furan-2-carboxylc acid (FFCA) as a key intermediate:

In one embodiment, streams routed to the primary oxidization zone 125 include a gas stream 10 comprising oxygen, a stream 20 comprising the solvent, and a stream 30 comprising the 5-HMF compound. The catalyst system may be introduced separately (not shown), or through streams 20 or 30, or both. In another embodiment, the oxidation solvent, the gas comprising oxygen, the catalyst system, and the 5-HMF compound can be fed to the primary oxidization zone 125 as separate, individual streams or can be combined in any combination prior to entering the primary oxidization zone 125. These streams may enter the primary oxidization zone 125 at a single location or at multiple locations.

In one embodiment, the primary oxidization off-gas stream 120 can have an oxygen content of less than 10 mole % in the continuous gas phase. Temperature of the stream 120 can range from 107° C. to 182° C., or from 112° C. to 162° C. The amount of solvent vapor in the off-gas stream 120 can range from 55% to 85%, from 60% to 80%, or from 70% to 78% by weight.

The process according to the invention next comprises (B) treating the primary oxidation off-gas stream 120 in an oxidizer off-gas treatment zone 825 according to a treating method of the invention.

Figure 2:
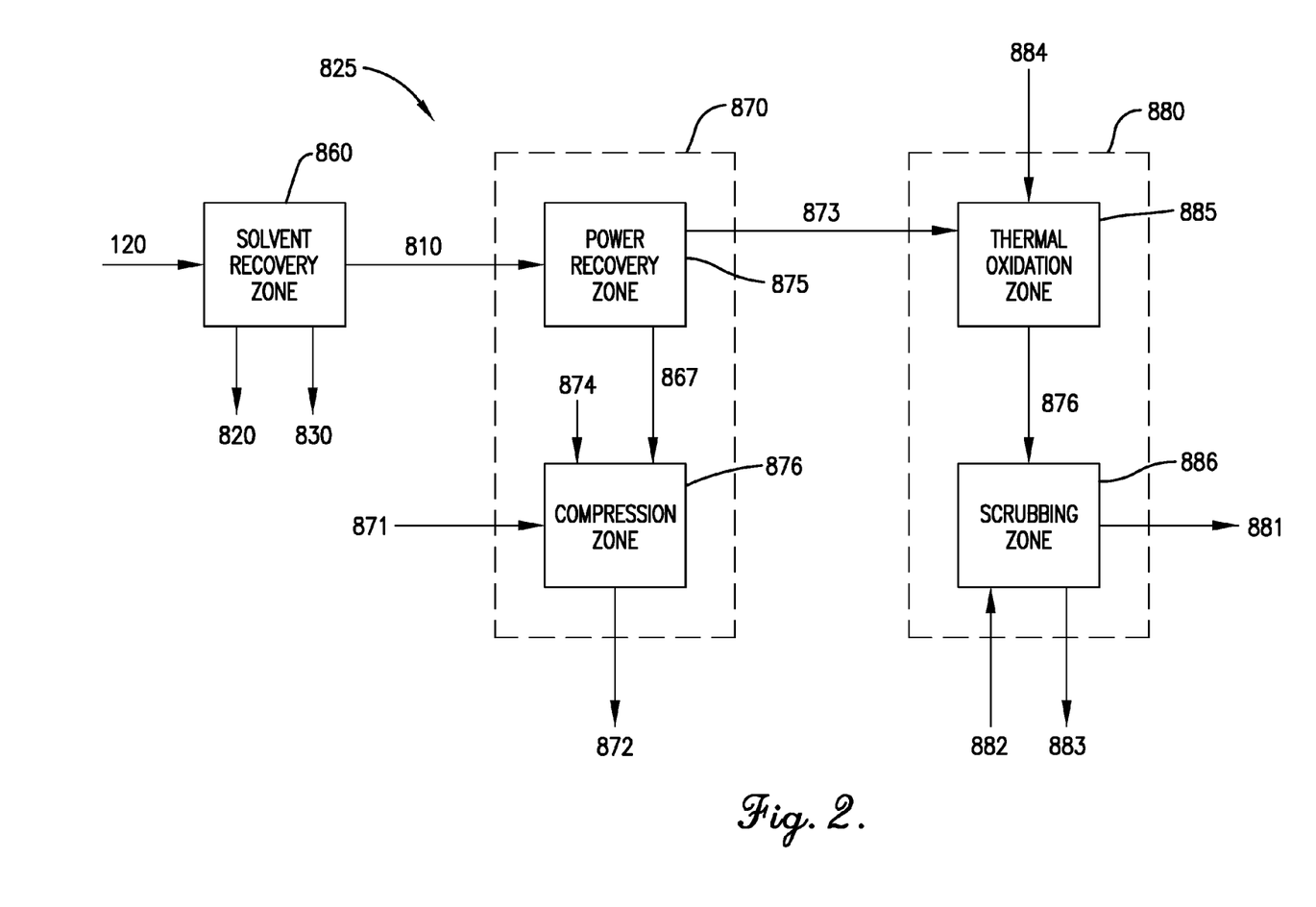
FIG. 2 is a flow diagram depicting a method for treating an oxidation off-gas stream from a process for producing a carboxylic acid product comprising FDCA according to the invention.

Details of the oxidizer off-gas treatment zone 825 are illustrated in FIG. 2. The treatment zone 825 comprises a solvent recovery zone 860, a power recovery and compression zone 870, and a gas-cleaning zone 880.

The off-gas treating method according to the invention comprises (B1) passing the primary oxidation off-gas stream 120 to the solvent recovery zone 860 to condense at least a portion of the solvent and water vapors in the off-gas stream 120 and to separate the stream 120 into a high-energy inert gas stream 810, a water-rich stream 820, and a solvent-rich stream 830.

Equipment suitable for use in the solvent recovery zone 860 include one or more distillation columns. The columns may contain packing, trays, or both. In addition, the distillation columns may operate with or without a reboiler.

By "high-energy," it is meant that the inert gas stream 810 has a higher temperature, a higher pressure, or both compared to low-energy inert gas stream 873.

By "water-rich," it is meant that stream 820 contains a higher concentration of water than the solvent-rich stream 830. The water-rich stream 820 preferably comprises greater than 60 wt % of water. It may be recycled to any location in the process where a water-rich stream is needed, or it may exit the process.

By "solvent-rich," it is meant that stream 830 contains a higher concentration of solvent than the water-rich stream 820. The solvent-rich stream 830 comprises water and solvent. The solvent-rich stream 830 typically comprises from 4% to 25%, 4% to 20%, 5% to 15%, 7°A) to 13%, 8% to 12%, 9% to 11%, 8% to 25%, or 7% to 25% by weight of water. The solvent-rich stream 830 can be recycled to any location in the process, or it can exit the process.

Referring again to FIG. 1, in one embodiment, at least a portion of the solvent-rich stream 830 is routed to a solid-liquid separation zone 625 where it is utilized as a wash to displace mother liquor from solids present in the separation zone 625. In another embodiment, at least a portion of the recovered solvent stream 830 is routed to wash feed stream 620, and the combined stream is routed to the separation zone 625 for the purpose of washing the solids present in the separation zone 625. In yet another embodiment, at least a portion of the stream 830 is routed back to the primary oxidation zone 125. In yet another embodiment, a portion of the stream 830 is routed back to the primary oxidation zone 125, and another portion of the stream 830 is routed to the separation zone 625.

Referring again to FIG. 2, the high-energy inert gas stream 810 is generated as an overhead stream in the solvent recovery zone 860. In one embodiment, at least a portion of the high-energy inert gas stream 810 is routed to a power recovery and compression zone 870. In another embodiment, at least a portion of stream 810 is used in the process as a conveying gas for moving solids through a conduit. In yet another embodiment, at least a portion of stream 810 is used as an inert gas to create an inert vapor phase in process vessels.

As illustrated in FIG. 2, the power recovery and compression zone 870 comprises a power recovery zone 875 and a compression zone 876. The off-gas treating method according to the invention next comprises (B2) passing the high-energy inert gas stream 810 to the power recovery zone 875 to convert the stream 810 to a low-energy inert gas stream 873 and to generate an electrical power stream 867.

By "low-energy", it is meant that the inert gas stream 873 has a lower temperature, a lower pressure, or both compared to the high-energy inert gas stream 810.

Equipment suitable for generating electrical power from stream 810 includes a turbo-expander. The energy recovered from a turbo-expander can be converted to electrical power by driving a rotating electrical generator connected to a power distribution and consuming network.

The off-gas treating method of the invention next comprises (B3) passing the electrical power stream 867 to a compression zone 876 to convert a low-pressure gas stream 871 comprising oxygen (such as atmospheric air) to a high-pressure gas stream 872 comprising oxygen.

By "low-pressure," it is meant that the stream 871 has a lower pressure than the stream 872. Typically, the stream 871 is at, slightly above, or slightly below atmospheric pressure.

By "high-pressure," it is meant that the stream 872 has a higher pressure than the stream 871. Typically, the stream 872 has a pressure greater than atmospheric, and can be as high as or higher than the pressure in the oxidation reaction zones 125, 335.

The compression zone 876 may draw power from an externally sourced power stream 874, if power from stream 867 is insufficient to drive the one or more compressors in the zone.

Turning back to FIG. 1, in one embodiment, at least a portion of the high-pressure gas stream 872 is routed to the primary oxidation zone 125.

In another embodiment, at least a portion of the high-pressure gas stream 872 is routed to the secondary oxidation zone 335. In yet another embodiment, at least a portion of portion of the high-pressure gas stream 872 is routed to both the primary and the secondary oxidation zones 125, 335.

Referring again to FIG. 2, the gas-cleaning zone 880 comprises a thermal oxidation zone 885 and a scrubbing zone 886. The off-gas treating method according to the invention next comprises (B4) passing the low-energy gas stream 873 and a stream 884 comprising an oxidizable fuel and oxygen to the thermal oxidation zone 885 to burn at least a portion of the organic compounds present in stream 873 and to generate a thermal oxidation gas stream 876.

Examples of oxidizable fuels include hydrogen, natural gas, and other hydrocarbon sources such as $C_1$-$C_8$ alkanes.

Next, the off-gas treating method according to the invention comprises (B5) passing the thermal oxidation gas stream 876 to a scrubbing zone 886 where it is contacted with a scrubbing liquid stream 882 comprising water, to generate a treated off-gas stream 881 and a liquid scrubbing effluent stream 883 comprising water.

The scrubbing zone 886 can employ one or more scrubbing units. Examples of suitable scrubbing units include vertical towers with counter-current contact of gas stream(s) with liquid stream(s).

The treated off-gas stream 881 can be discharged to the atmosphere. Alternatively, at least a portion of the stream 881 can be used as an inert gas stream in the process for providing an inert gas atmosphere in process unit operations. In another embodiment, at least a portion of the gas stream 881 can be used as a conveying gas to convey solids in a conduit.

Turning back to FIG. 1, the process according to the invention next comprises (C) passing at least a portion of the crude carboxylic acid slurry stream 110 and a fresh organic acid solvent stream 220 to a liquid displacement zone 225 to produce a displaced mother liquor stream 230 and a low-impurity carboxylic acid slurry stream 210 comprising FDCA and FFCA. The displaced mother liquor stream 230 comprises solvent, impurities, and catalyst components.

In one embodiment, from 5% to 99%, from 30% to 95%, or from 50 to 95% by weight of the mother liquor present in the crude carboxylic slurry stream 110 is displaced in the liquid displacement zone 225. Sufficient fresh solvent is fed to the liquid displacement zone 225 via stream 220 such that the low impurity slurry stream 210 can be pumped. The slurry stream 210 preferably comprises from 1% to 50%, 10% to 40%, or from 25% to 38% by weight of solids. The liquid displacement zone 225 may be accomplished in a single unit operation or multiple unit operations.

In one embodiment, the liquid displacement zone 225 comprises a solid-liquid separation device capable of generating an isolated wet cake from a feed slurry and a separate mixing device capable of mixing the isolated wet cake with fresh solvent to generate the low impurity stream 210. Examples of suitable solid-liquid separation devices include a continuous-pressure drum filter, solid-bowl centrifuges including decanter and disc-stack centrifuge, and batch-pressure filters including candle and leaf filters. The preferred solid-liquid separation device is a continuous-pressure drum filter. The solid-liquid separator can be operated at temperatures from 30° C. to 200° C., or more typically from 80° C. to 170° C. The solid-liquid separator in the liquid displacement zone 225 may be operated in continuous or batch mode, although it will be appreciated that for commercial processes, the continuous mode is preferred.

Alternatively, a portion of the mother liquor in stream 110 is displaced with fresh solvent stream 220 in a single device to form the low impurity slurry stream 210 without forming an isolated wet cake.

In one embodiment, from 5% to 100% by weight of the displaced mother liquor stream 230 is routed to a purge zone 235 to separate impurities in the stream 230 from the solvent and catalyst components. The separated impurities exit the process as purge stream 920. The separated solvent and catalyst are recycled to the process via stream 910.

In one embodiment, the recovered solvent stream 910 is recycled to the primary oxidization zone 125. The stream 910 preferably contains at least 30%, at least 50%, at least 70%, or at least 90% by weight of the catalyst that entered the purge zone 235 from the stream 230.

In another embodiment of this invention, a portion (up to 100% by weight) of the crude carboxylic acid slurry stream 110 may be routed directly to a secondary oxidation zone 335 without being subjected to the liquid displacement zone 225.

In another embodiment, up to 100 wt % of the feed to the purge zone 235 may be a mother liquor stream 630 generated in the solid-liquid separation zone 625. In yet another embodiment, up to 100 wt % of the feed to the purge zone 235 may be a mother liquor stream generated in a secondary liquid displacement zone (not shown) located at a location downstream of the secondary oxidation zone 335. The secondary liquid displacement zone may include equipment like those described for the liquid displacement zone 225.

The process according to the invention next comprises (D) passing the low-impurity slurry stream 210, if the liquid displacement zone 225 is employed, to a secondary oxidation zone 335. In the secondary oxidation zone 335, the low-impurity product stream 210, the crude product stream 110, or both are contacted with oxygen at conditions effective to oxide the FFCA in those streams to form a secondary oxidation product stream 310 comprising additional FDCA.

Oxygen to the secondary oxidation zone 335 is provided by line 320 and may be in the form of an oxygen-containing gas, such as air, purified air, oxygen-enriched air, or even pure oxygen gas.

The secondary oxidation zone 335 comprises at least one oxidation reactor vessel.

Generally, the secondary oxidation zone may be operated at a temperature ranging from 115° C. to 220° C., or from 120° C. to 200° C. Preferably, oxidation in the secondary oxidation zone 335 is conducted at a higher temperature than the oxidation in the primary oxidation zone 125 to enhance impurity removal. In one embodiment, the secondary oxidation zone 335 is operated at 10° C., 20° C., or 30° C. higher than the oxidation temperature in the primary oxidation zone 125 to enhance impurity removal.

The secondary oxidation zone 335 can be heated directly with solvent vapor or steam via stream 320 or indirectly by any means known in the art.

The pressure in the secondary oxidation zone 335 can range from 0.2 to 1.6 MPa, and preferably from 0.2 to 1.0 MPa.

Additional purification of the low impurity slurry stream 210 is accomplished in the secondary oxidation zone 335 by a mechanism involving oxidation of impurities and intermediates including FFCA, and recrystallization or crystal growth. One of the functions of the secondary oxidation zone 335 is to convert FFCA to FDCA. FFCA is considered mono-functional relative to a polyester condensation reaction, because it contains only one carboxylic acid. FFCA is present in the crude carboxylic acid stream 110 and the low impurity slurry stream 210. FFCA is generated in the primary oxidation zone 125, because the reaction of 5-HMF to FFCA can be about eight times faster than the reaction of FFCA to the desired di-functional product FDCA.

As mentioned above, additional air or molecular oxygen is fed via stream 320 to the secondary oxidation zone 335 in an amount necessary to oxidize a substantial portion of the partially oxidized products such as FFCA in the stream 210 to the corresponding carboxylic acid FDCA. Generally, at least 70%, but preferably at least 80%, and more preferably at least 90% by weight of the FFCA present in the low impurity slurry stream 210 is converted to FDCA in the secondary oxidation zone 335.

Significant concentrations of mono-functional molecules like FFCA in the dry, purified FDCA product are particularly detrimental to polymerization processes as they may act as chain terminators during the polyester condensation reaction.

The amount of oxygen fed in the secondary oxidation zone 335 is controlled to limit burning organic molecules to $CO_2$. The amount of oxygen in secondary oxidation zone off-gas stream 330 can be monitored and used to control the amount of oxygen fed via stream 320.

Another function of the secondary oxidation zone 335 is to dissolve and recrystallize solids present in the low impurity slurry stream 210. At least 10%, at least 25%, at least 50%, or preferably at least 85% by weight of solid impurities and oxidation by-products in the stream 210 go into solution, as the FDCA particles are dissolved and re-crystallized in the secondary oxidation zone 335.

Off-gas from the secondary oxidation zone 335 is withdrawn via line 330. The off-gas stream 330, which comprises solvent vapor and volatile organic compounds (VOCs), can be fed to a recovery system (not shown) to separate the solvent from the VOCs. VOCs including methyl bromide may subsequently be treated, for example, by incineration in a catalytic oxidation unit.

The process according to the invention next comprises (E) passing at least a portion of the secondary oxidation product stream 310 to a crystallization zone 425, to a cooling zone 430, or to both to produce a cooled, crystallized product stream 510. In one embodiment, the secondary oxidation slurry 310 is passed to a crystallization zone 425 to form a crystallized slurry stream 410. Generally, the crystallization zone 425 comprises at least one crystallizer.

The crystallization zone 425 produces an off-gas, which is removed via line 420. The off-gas stream 420, which comprises solvent vapor and VOCs, can be routed to a recovery system where the solvent is separated from the VOCs (not shown). For example, the solvent vapor in the off-gas stream 420 can be condensed in at least one condenser and returned to the crystallization zone (not shown). Alternatively, the solvent vapor in stream 420 can be withdrawn or sent to an energy recovery device (not shown). The VOCs may be treated, for example, by incineration in a catalytic oxidation unit.

The crystallization zone 425 may be operated at a temperature ranging from 40° C. to 175° C., preferably from 50° C. to 170° C., and more preferably from 60° C. to 165° C.

The crystallized product stream 410 is then passed to the cooling zone 430 to generate the cooled, crystallized product slurry stream 510. The crystallized slurry stream 410 can be cooled by any means known in the art; typically, the cooling zone 430 comprises a flash tank. The temperature of the stream 510 can range from 35° C. to 160° C., from 45° C. to 120° C., and preferably from 55° C. to 95° C.

In another embodiment, a portion (up to 100 wt %) of the secondary oxidation slurry stream 310 is routed directly to the cooling zone 430; thus, that portion is not subjected to crystallization in the crystallization zone 425.

In yet another embodiment, a portion (up to 100 wt %) of the crystallized slurry stream 410 may be passed directly to a secondary liquid displacement zone (not shown). Up to 100 wt % of the slurry effluent comprising FDCA from such a secondary liquid displacement zone can be routed to the solid-liquid separation zone 625 and/or routed directly to the cooling zone 430. The function of the secondary liquid displacement zone is to displace a portion (e.g., ≥5% by weight) of the solvent in the crystallized slurry stream 410 with fresh solvent and/or water. The secondary liquid displacement zone, if employed, would be separate and distinct from the liquid displacement zone 225. The same type of equipment may be used for both the primary (225) and secondary liquid displacement zones.

In yet another embodiment, the crystallized slurry stream 410 may be passed directly to the solid-liquid separation zone 625 without being first processed in the cooling zone 430.

The process according to the invention next comprises (F) passing the cooled crystallized product stream 510 to the solid-liquid separation zone 625 to separate solids from liquids; to wash the separated solids with a wash solvent 620, 830; and to reduce moisture in the washed solids to obtain a purified, de-watered wet cake stream 610 and a solid-liquid separation mother liquor stream 640 comprising the solvent, catalyst components, impurities, and oxidation products. These functions may be accomplished in one or more solid-liquid separation devices. The solid-liquid separation zone 625 comprises at least one solid-liquid separation device capable of separating solids and liquids, washing solids with a wash fed stream 620, and reducing the moisture content in the washed solids to less than 30 weight %, to less than 25 weight %, to less than 20 weight %, to less than 15 weight %, or preferably to less than 10 weight %.

The solid-liquid separation zone 625 comprises one or more solid-liquid separation devices. Equipment suitable for use in the solid-liquid separation zone 625 typically includes centrifuges such as solid-bowl centrifuges, disc-stack centrifuges, and decanter centrifuges; cyclones; and filters such as pressure-drum filters, vacuum-drum filters, belt filters including vacuum-belt filters, rotary-drum filters, pressure-leaf filters, candle filters, etc. The preferred solid-liquid separation device for the solid-liquid separation zone 625 is a rotary, pressure-drum filter.

The temperature of the cooled slurry stream 510 can range from 50° C. to 140° C., from 70° C. to 120° C., or preferably from 75° C. to 95° C.

The wash stream 620 comprises a liquid suitable for displacing and washing mother liquor from the solids. In one embodiment, the wash solvent comprises acetic acid and water. In another embodiment, the wash solvent comprises up to 100 wt % of water. The temperature of the wash solvent stream 620 can range from 20° C. to 120° C., from 40° C. to 110° C., or preferably from 50° C. to 90° C. The amount of wash solvent used can be defined by the wash ratio, which is the mass of the wash solvent divided by the mass of the solids on a batch or continuous basis. The wash ratio can range from 0.3 to 5, from 0.4 to 4, or preferably from 0.5 to 3.

After the solids are washed in the solid-liquid separation zone 625, they are dewatered. Dewatering involves reducing the moisture content of the solids to form the purified, dewatered wet cake stream 610. In one embodiment, dewatering is accomplished in a filter by passing a gas stream through the solids to displace free liquid after the solids have been washed with a wash solvent. In another embodiment, dewatering is achieved by centrifugal forces in a perforated-bowl or a solid-bowl centrifuge.

Stream 630 generated in the solid-liquid separation zone 625 is a mother liquor stream comprising solvent, catalyst, and some impurities and oxidation by-products. In one embodiment, a portion of the stream 630 is routed to the purge zone 235. In another embodiment, a portion (e.g., 5 wt %) of the stream 630 is routed back to the primary oxidation zone 125 (not shown).

Wash liquor stream 640 is also generated in the solid-liquid separation zone 625. The stream 640 comprises a portion of the mother liquor present in stream 510 and wash solvent. The ratio of mother liquor mass to wash solvent mass may be less than 3, and preferably less than 2.

The process according to the invention next comprises (G) passing the purified, de-watered wet cake stream 610 to a drying zone 725 to dry the wet cake stream 610 and obtain a dry, purified carboxylic product stream 710 comprising FDCA. The drying zone 725 also generates a vapor stream 720.

In one embodiment, the vapor stream 720 comprises wash solvent vapor. In another embodiment, the vapor stream 720 comprises oxidation solvent and wash solvent vapors.

The drying zone 725 comprises at least one dryer and can be accomplished by any means known in the art that is capable of evaporating at least 10 wt % of the volatiles remaining in the purified, dewatered wet cake stream 610 to produce the dry product stream 710 comprising purified FDCA and the vapor stream 720. Examples of suitable dryers include indirect-contact dryers including a rotary, steam-tube dryer; a Single-Shaft Porcupine® dryer; and a Bepex Solidaire® dryer. Direct-contact dryers including a fluidized-bed dryer can also be used. Drying can also be achieved in a conveying line.

The dried product stream 710 comprises purified FDCA with less than 8 wt % moisture. Preferably, the purified FDCA contains less than 5 wt %, less than 1 wt %, less than 0.5 wt %, or less than 0.1 wt % moisture. In an embodiment of this invention, if the liquid portion of the purified dewatered wet cake stream 610 comprises water and less than 0.1 weight %, less than 500 ppm wt, or less than 200 ppm wt of acetic acid; the stream 610 can be fed directly to a polymerization zone without first being dried.

The dried, carboxylic acid product in stream 710 can have a b* color value of less than 9, less than 6, less than 5, less than 4, or less than 3. The b* color value is one of the three-color attributes measured on a spectroscopic reflectance-based instrument. Typically, the measuring device is a Hunter Ultrascan XE instrument in reflectance mode. Positive readings signify the degree of yellow (or absorbance of blue), while negative readings signify the degree of blue (or absorbance of yellow).

In a preferred embodiment, the process according to the invention produces a carboxylic acid composition comprising at least 95 wt % of FDCA and less than 1000 ppm of FFCA, and having a b* value of less than 9. In other preferred embodiments, the carboxylic acid composition comprises at least 96 wt %, at least 98 wt %, at least 99 wt %, or at least 99.5 wt % of FDCA; and less than 900 ppm, less than 500 ppm, less than 250 ppm, less than 100 ppm, or less than 10 ppm of FFCA; and has a b* value of less than 6, less than 5, less than 4, or less than 3.

Each embodiment of the process according to the invention can optionally comprise an additional step of decolorizing of the FDCA or esterifying the FDCA with a diol stream via hydrogenation. The diol stream may comprise ethylene glycol or isomers of cyclohexane diol, preferably the 1,4-cyclohexane diol isomer. The decolorizing or esterifying step can be accomplished by any means known in the art and is not limited to hydrogenation. For example, the decolorizing step can be accomplished by reacting a carboxylic acid—which has undergone esterification treatment, for example, with ethylene glycol—with molecular hydrogen in the presence of a hydrogenation catalyst in a reaction zone to produce a decolorized carboxylic acid solution or a decolorized ester product. For the reactor zone, there are no special limitations in the form or construction thereof, subject to an arrangement that allows a supply of hydrogen to intimately contact the carboxylic acid or ester product with the catalyst in the reaction zone. Typically, the hydrogenation catalyst is a single Group VIII metal or combination of Group VIII metals. Preferably, the catalyst is selected from a group consisting of palladium, ruthenium, rhodium, and combinations thereof. The reaction zone comprises a hydrogenation reactor that operates at a temperature and pressure sufficient to hydrogenate a portion of the characteristically yellow compounds to colorless derivatives.

As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered to be approximations. These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 50 to 100 is intended to include all values within the range including sub-ranges such as 60 to 90 and 70 to 80.

This invention can be further illustrated by the following examples of preferred embodiments thereof, although it will be understood that these examples are included merely for purposes of illustration and are not intended to limit the scope of the invention. Unless otherwise indicated, all percentages are by weight.

EXAMPLES

Analytical

Gas Chromatographic Method

Process samples were analyzed using a Shimadzu gas chromatograph Model 2010 (or equivalent) equipped with a split/heated injector (300° C.) and a flame ionization detector (300° C.). A capillary column (60 meter×0.32 mm ID) coated with (6% cyanopropylphenyl)-methylpolysiloxane at 1.0 µm film thickness (such as DB-1301 or equivalent) was employed. Helium was used as the carrier gas with an initial column head pressure of 29.5 psi and an initial column flow of 3.93 mL/minute while the carrier gas linear velocity of 45 cm/second was maintained constant throughout the entire oven temperature program.

The column temperature was programmed as follows: The initial oven temperature was set at 80° C. and was held for 6 minutes; the oven was ramped up to 150° C. at 4° C./minute and was held at 150° C. for 0 minute; the oven was ramped up to 240° C. at 10° C./minute and was held at 240° C. for 5 minutes; then the oven was ramped up to 290° C. at 10° C./minute and was held at 290° C. for 17.5 minutes (the total run time was 60 mins).

1.0-µL of the prepared sample solution was injected with a split ratio of 40:1. EZ-Chrom Elite chromatography data system software was used for data acquisition and data processing.

The sample preparation was done by weighing 0.1 g (accurate to 0.1 mg) of sample in a GC vial and adding 200.0 µL ISTD solution (1% by volume of decane in pyridine) and 1000 µL of BSTFA (N,O-bis(trimethylsilyl)trifluoroacetamide) with 1% TMSCl (trimethylchlorosilane) to the GC vial. The content was heated at 80° C. for 30 minutes to ensure complete derivatization. 1.0-µL of this prepared sample solution was injected for GC analysis.

Liquid Chromatographic Method for Low Level Measurement of FFCA in FDCA

Samples are analyzed with an Agilent 1200 LC unit consisting of a quaternary pump, an autosampler (3 uL injection), a thermostated column compartment (35 C), and a diode array UV/vis detector (280 nm). The chromatograph is fitted with a 150 mm×4.6 mm Thermo Aquasil C18 column packed with 5 micron particles. The solvent flow program is shown in the table below where channel A is 0.1% phosphoric acid in water, channel B is acetonitrile, and channel C is tetrahydrofuran (THF).

| Time (min) | % A | % B | % C | Flow (ml/min) |
|---|---|---|---|---|
| Initial | 95.0 | 0.0 | 5.0 | 1.50 |
| 7 | 95.0 | 0.0 | 5.0 | 1.50 |
| 10 | 15.0 | 80.0 | 5.0 | 1.50 |
| 12 | 15.0 | 80.0 | 5.0 | 1.50 |
| 12.1 | 95.0 | 0.0 | 5.0 | 1.50 |
| 15 | 95.0 | 0.0 | 5.0 | 1.50 |

Equilibration time: 1 minute

EZChrom elite was used for control of the HPLC and for data processing. A 5 point linear calibration was used in the (approximate) range of 0.25 to 100 ppm FFCA.

Samples were prepared by dissolving ~0.05 g (weighed accurately to 0.0001 g) in 10 ml of 50:50 DMF/THF; higher sample weights may have been used for samples where the FFCA was present at a very low level, provided that the solubility of FDCA was not exceeded. Sonication was used to ensure complete dissolution of the sample in the solvent. A portion of the prepared sample was transferred to an auto sampler vial for injection onto the LC.

Color Measurement

1) Assembled the Carver Press die as instructed in the directions—placed the die on the base and placed the bottom 40 mm cylinder polished side face-up.

2) Placed a 40 mm plastic cup (Chemplex Plasticup, 39.7× 6.4 mm) into the die.

3) Filled the cup with the sample to be analyzed. The exact amount of sample added was not important.

4) Placed the top 40 mm cylinder polished side face-down on the sample.

5) Inserted the plunger into the die. No "tilt" should have been exhibited in the assembled die.

6) Placed the die into the Carver Press, making sure that it was near the center of the lower platen. Closed the safety door.

7) Raised the die until the upper platen makes contact with the plunger. Applied >20,000 lbs pressure. Then allowed the die to remain under pressure for approximately 3 minutes (exact time not critical).

8) Released the pressure and lowered the lower platen holding the die.

9) Disassembled the die and removed the cup. Placed the cup into a labeled plastic bag (Nasco Whirl-Pak 4 oz).

10) Using a HunterLab Colorquest XE colorimeter, created the following method (Hunterlab EasyQuest QC software, version 3.6.2 or later):
Mode: RSIN-LAV (Reflectance Specular Included-Large Area View)
Measurements:
CIE L* a* b*
CIEXYZ 11) Standardized the instrument as prompted by the software using the light trap accessory and the certified white tile accessory pressed against the reflectance port.

12) Ran a green tile standard using the certified white tile and compared the CIE X, Y, and Z values obtained against the certified values of the tile. The values obtained should have been ±0.15 units on each scale of the stated values.

13) Analyzed the sample in the bag by pressing it against the reflectance port and obtaining the spectrum and L*, a*, b* values. Obtained duplicate readings and average the values for reporting.

Examples 1-2

Air oxidations of 5-HMF using a cobalt, manganese, and ionic bromine catalyst system in an acetic acid solvent were conducted in a reactor at 130 psig and 110-160° C. After reaction, the heterogeneous mixture was filtered to isolate the crude FDCA. The crude FDCA was washed with acetic acid two times and then twice with deionized water. The washed crude FDCA was oven dried at 110° C. under vacuum overnight. The solid and the filtrate were analyzed by Gas Chromatography using BSTFA derivatization method. b* value of the solid was measured using a Hunter Ultrascan XE instrument. The results are shown in Table 1 below.

TABLE 1

|  | Example 1a | Example 1b | Example 2a | Example 2b |
| --- | --- | --- | --- | --- |
| Bromine Source | solid NaBr | solid NaBr | aqueous NaBr | aqueous NaBr |
| Co Concentration (ppm) | 2000 | 2000 | 2000 | 2000 |
| Mn Concentration (ppm) | 93.3 | 93.3 | 93.3 | 93.3 |
| Br Concentration (ppm) | 3000 | 3000 | 3000 | 3000 |
| FDCA Yield (wt %) | 81.6 | 82.6 | 89.4 | 88.6 |

TABLE 1-continued

|  | Example 1a | Example 1b | Example 2a | Example 2b |
| --- | --- | --- | --- | --- |
| FFCA Yield (wt %) | 0.81 | 0.87 | 0.58 | 0.8 |
| CO (total mol) | 0.013 | 0.013 | 0.003 | 0.0037 |
| $CO_2$ (total mol) | 0.078 | 0.092 | 0.061 | 0.061 |
| $CO + CO_2$ (×$10^{-4}$ mol/min) | 7.58 | 8.75 | 5.33 | 5.39 |
| Color (b*) | 13.91 | 14.14 | 5.845 | 6.175 |

As seen in Table 1, it is possible to generate yields of FDCA of up to 89.4 wt %, b*<6, and low carbon burn (<0.0006 mol/min $CO+CO_2$).

Examples 3-4

Glacial acetic acid, crude FDCA which contains some FFCA, and the catalyst components in the concentrations report in Tables 2 and 3 below were transferred to a 300 mL titanium autoclave equipped with a high pressure condenser and a baffle. Cobalt, manganese, and ionic bromine were provided as cobalt (II) acetate tetrahydrate, manganese (II) acetate, and sodium bromide and/or aqueous hydrobromic acid, respectively. The autoclave was pressurized with approximately 50 psig of nitrogen, and the reaction mixture was heated to the desired temperature in a closed system (i.e., with no gas flow) with stirring.

At the listed reaction temperature and 130 psig, an air flow of 1500 sccm was introduced at the bottom of the solution, and the reaction pressure was adjusted to the desired pressure. After 30 seconds from the start of air feeding, 1.0 g of peracetic acid in 5.0 mL of acetic acid was introduced using a blow-case to start the reaction. The reaction was continued for a desired period of time. At which time, the air flow was stopped, and the autoclave was cooled to room temperature and depressurized. The heterogeneous mixture was filtered to isolate the pFDCA. The mass of the filtrate was recorded.

The pFDCA was washed with 60 mL of acetic acid two times and then twice with 100 mL of deionized water. The washed pFDCA was oven dried at 110° C. under vacuum overnight and then weighed. The solid was analyzed by Gas Chromatography using BSTFA derivatization method, HPLC, and color measurement (b*) methods. The filtrate was analyzed by Gas Chromatography using BSTFA derivatization method only.

The off-gas was analyzed for CO and $CO_2$ by ND-1R (ABB, Advanced Optima) and $O_2$ by a paramagnetism detection system (Servomex, 1440 Model).

The results are shown in Tables 2 and 3 below.

TABLE 2

| Example No. | Reaction Temp. (° C.) | Reaction Time (hr) | Co (ppm w) | Mn (ppm w) | Br (ppm w) | FFCA (ppm) | b* | CO (×$10^{-3}$ total mol) | $CO_2$ (×$10^{-2}$ total mol) | $CO + CO_2$ (×$10^{-4}$ mol/min) |
| --- | --- | --- | --- | --- | --- | --- | --- | --- | --- | --- |
| 3a | 175 | 2 | 225 | 10.7 | 225 | <10 | 3.56 | 2 | 1.64 | 1.5 |
| 3b | 200 | 1 | 300 | 14.2 | 300 | <10 | 4.04 | 2.1 | 1.14 | 2.3 |
| 3c | 200 | 3 | 300 | 14.2 | 300 | <10 | 3.18 | 3.9 | 1.664 | 1.1 |
| 3d | 175 | 2 | 225 | 10.7 | 225 | <10 | 3.21 | 3 | 2.02 | 1.9 |
| 3e | 150 | 1 | 150 | 7.2 | 150 | 1900 | 7.19 | 1.34 | 0.633 | 1.3 |
| 3f | 150 | 1 | 300 | 14.2 | 300 | 1400 | 6.55 | 0.72 | 0.628 | 1.2 |
| 3g | 175 | 2 | 225 | 10.7 | 225 | <10 | 4.13 | 2.1 | 1.58 | 1.5 |
| 3h | 150 | 3 | 300 | 14.2 | 300 | 300 | 4.6 | 1.8 | 1.31 | 0.8 |
| 3i | 200 | 3 | 150 | 7.2 | 150 | <10 | 3.65 | 1.4 | 1.33 | 0.8 |
| 3j | 200 | 1 | 150 | 7.2 | 150 | <10 | 3.59 | 1.5 | 1.25 | 2.3 |
| 3k | 175 | 2 | 225 | 10.7 | 225 | <10 | 3.45 | 3.2 | 2.59 | 2.4 |
| 3l | 150 | 3 | 150 | 7.2 | 150 | 390 | 5.95 | 1.4 | 1.39 | 0.9 |

TABLE 3

| Example No. | Temp. (°C.) | Reaction Time (hr) | Co (ppm w) | Mn (ppm w) | Br (ppm w) | FFCA (ppm) | b* | CO ($\times 10^{-3}$ total mol) | $CO_2$ ($\times 10^{-2}$ total mol) | $CO + CO_2$ ($\times 10^{-4}$ mol/min) |
|---|---|---|---|---|---|---|---|---|---|---|
| 4a | 180 | 2 | 300 | 14.2 | 300 | <10 | 3.46 | 1 | 1.64 | 1.5 |
| 4b | 200 | 1 | 300 | 14.2 | 300 | 410 | 3.49 | 1.2 | 1.11 | 2.1 |

The invention has been described in detail with particular reference to preferred embodiments thereof, but it will be understood that variations and modifications can be effected within the spirit and scope of the invention.

We claim:

1. A method for treating an off-gas stream from a process for producing furan-2,5-dicarboxylic acid, the method comprising:
   (a) providing an off-gas stream comprising an acetic acid vapor, water vapor, and an inert gas from a primary oxidation zone of a process for producing furan-2,5-dicarboxylic acid;
   (b) passing the off-gas stream to a solvent recovery zone to condense and separate at least a portion of the organic acid solvent vapor and the water vapor to obtain a water-rich stream, a solvent-rich stream, and a high-energy inert gas stream;
   (c) passing the high-energy inert gas stream to a power recovery zone to convert the high-energy inert gas stream to a low-energy inert gas stream and to generate an electrical power stream;
   (d) passing the electrical power stream to a compression zone to convert a low-pressure gas stream comprising oxygen into a high-pressure gas stream comprising oxygen;
   (e) passing the low-energy inert gas stream and a stream comprising an oxidizable fuel and oxygen to a thermal oxidation zone to combust at least a portion of organic compounds in the low-energy inert gas stream and generate a thermal oxidation gas stream; and
   (f) passing the thermal oxidation gas stream to a scrubbing zone to generate a treated off-gas stream and a liquid scrubbing effluent stream comprising water; wherein said process for producing furan-2,5-dicarboxylic acid yield is greater than 90%.

2. The method according to claim 1, wherein the solvent recovery zone comprises a distillation column.

3. The method according to claim 1, wherein the solvent-rich stream comprises from 4 to 25% by weight of water.

4. The method according to claim 1, wherein the water-rich stream comprises at least 60% by weight of water.

5. The method according to claim 1, wherein the power recovery zone comprises a turbo-expander.

6. The method according to claim 1, which further comprises passing at least a portion of the high-pressure gas stream comprising oxygen to the primary oxidation zone.

7. The method according to claim 1, wherein the process for producing furan-2,5-dicarboxylic acid further comprises a secondary oxidation zone, and at least a portion of the high-pressure gas stream comprising oxygen is passed to the secondary oxidation zone.

8. The method according to claim 1, wherein the process for producing furan-2,5-dicarboxylic acid further comprises a solid-liquid separation zone, and at least a portion of the solvent-rich stream is passed to the solid-liquid separation zone to displace mother liquor from solids in the separation zone.

9. The method according to claim 8, wherein at least a portion of the solvent-rich stream is recycled to the primary oxidation zone.

10. The method according to claim 1, wherein at least a portion of the solvent-rich stream is recycled to the primary oxidation zone.

* * * * *